(12) United States Patent
Anderson et al.

(10) Patent No.: US 8,247,019 B2
(45) Date of Patent: Aug. 21, 2012

(54) COATING SLEEVE

(75) Inventors: Jonathan D. Anderson, Chanhassen, MN (US); Dale L. Anderson, Minnetrista, MN (US); Aaron J. Anderson, Chanhassen, MN (US)

(73) Assignee: Harland Medical Systems, Inc., Eden Prairie, MN (US)

( * ) Notice: Subject to any disclaimer, the term of this patent is extended or adjusted under 35 U.S.C. 154(b) by 1120 days.

(21) Appl. No.: 12/110,141

(22) Filed: Apr. 25, 2008

(65) Prior Publication Data

US 2008/0292777 A1 Nov. 27, 2008

Related U.S. Application Data

(60) Provisional application No. 60/913,951, filed on Apr. 25, 2007.

(51) Int. Cl.
*A61L 33/00* (2006.01)

(52) U.S. Cl. ...... 427/2.24; 623/1.46; 427/508; 427/595; 427/457; 427/389.9; 427/242

(58) Field of Classification Search ................. 427/2.24, 427/508, 595, 457, 389.9, 242; 623/1.46
See application file for complete search history.

(56) References Cited

U.S. PATENT DOCUMENTS

| 5,691,018 A | 11/1997 | Kelley et al. |
| 2004/0213893 A1 | 10/2004 | Boulais |
| 2005/0100655 A1 | 5/2005 | Zhong et al. |
| 2007/0075452 A1* | 4/2007 | Leeflang et al. ............. 264/129 |

* cited by examiner

*Primary Examiner* — Robert D. Harlan
(74) *Attorney, Agent, or Firm* — Patterson Thuente Christensen Pedersen, P.A.

(57) ABSTRACT

The present invention provides an apparatus and a method for modifying a structure such as a medical device through the selective application of a coating. A coating sleeve may comprise an elastomeric wall that may be permeable or impermeable to a coating material and may be porous so as to allow for patterned coating of the device. The coating sleeve may contain surface protrusions that facilitate manipulation by providing sites for grasping and pulling. In operation the coating sleeve may be fitted on the device prior to application of a coating and removed subsequent to application of the coating.

23 Claims, 5 Drawing Sheets

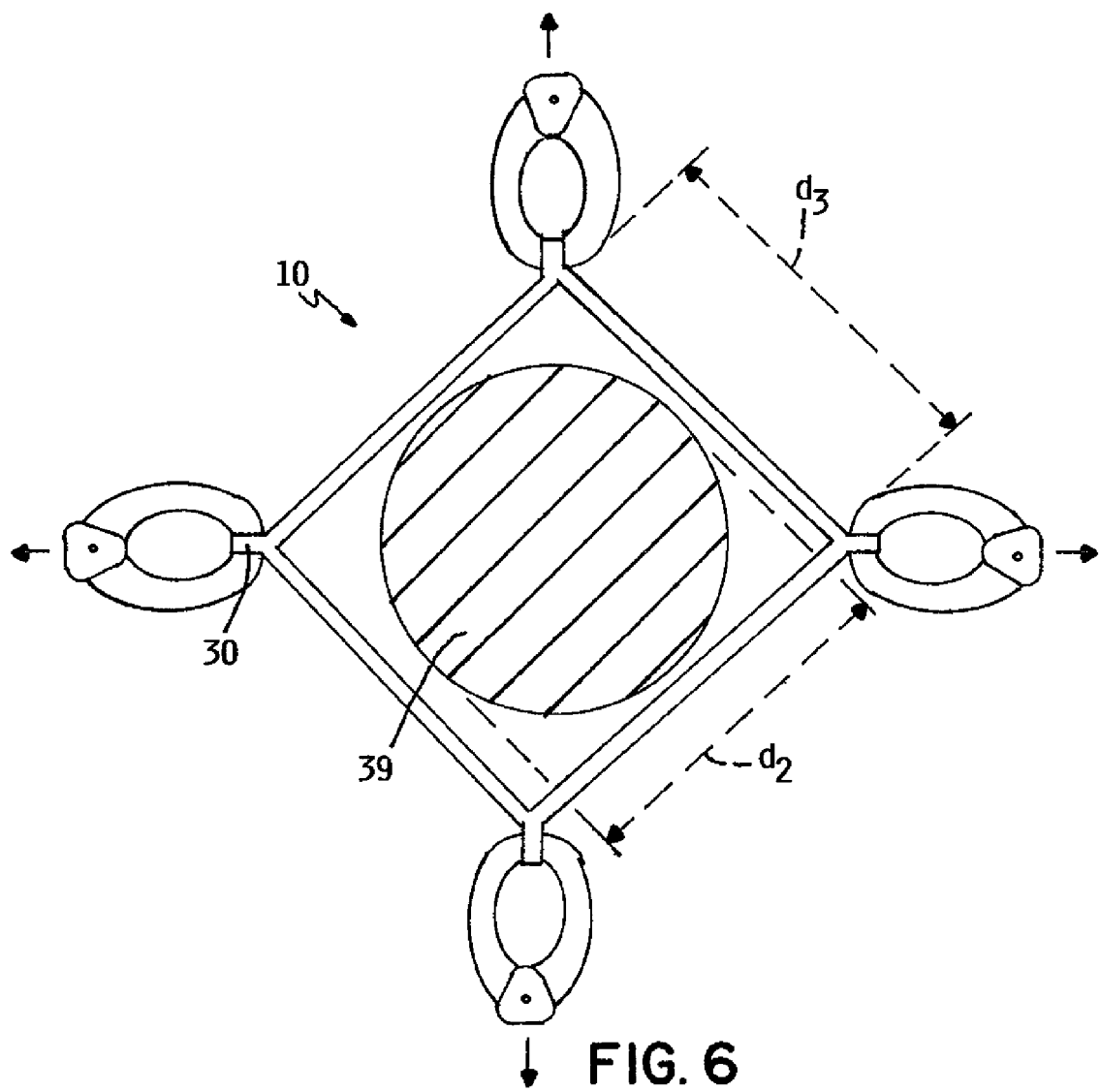
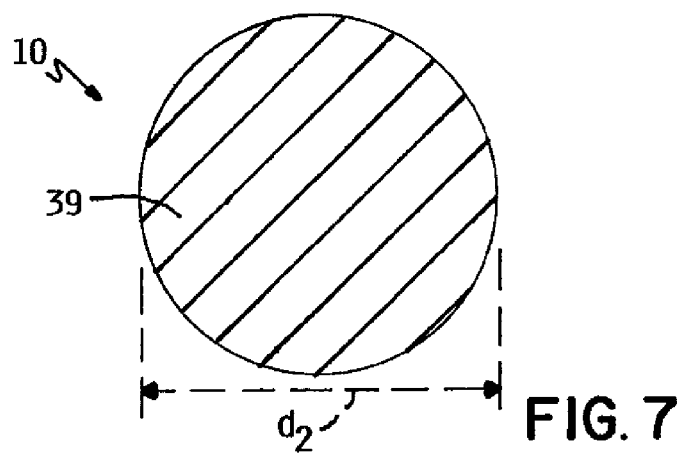

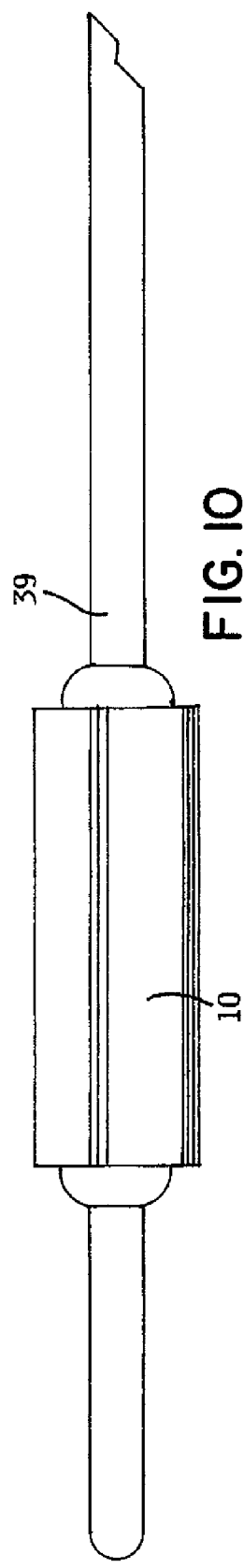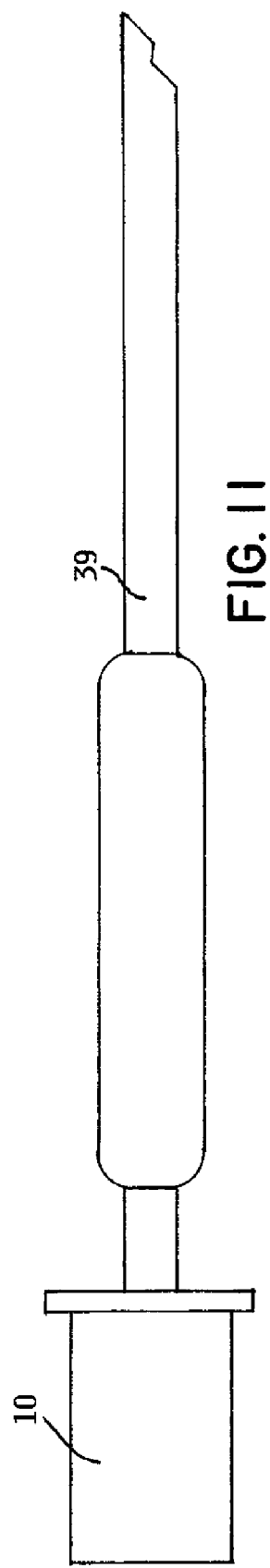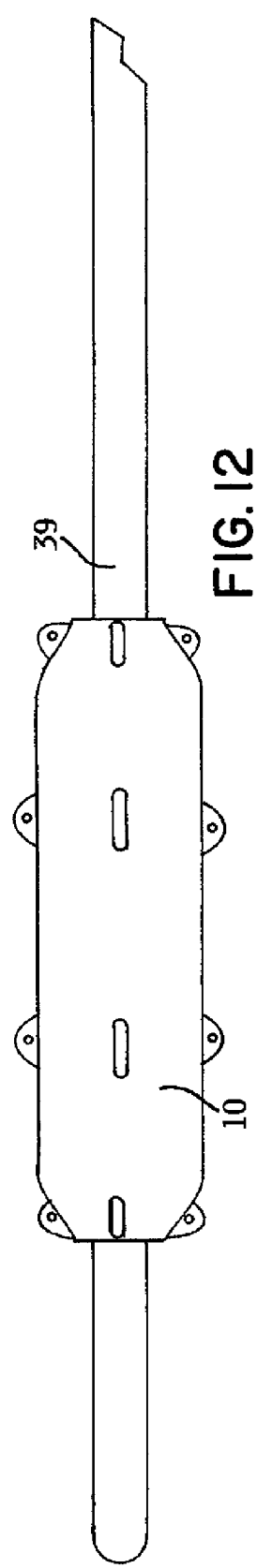

COATING SLEEVE

This application claims priority to U.S. Provisional Application No. 60/913,951 filed Apr. 25, 2007; said application is incorporated herein by reference.

FIELD OF THE INVENTION

The present invention relates generally to coated medical devices. More particularly, the present invention relates to an apparatus and method for selectively coating distinct regions of a medical device structure.

BACKGROUND OF THE INVENTION

The quality of medical care has been greatly enhanced by improvements to medical devices. However, the materials from which such medical devices may be made, as well as their structure and the manner in which they may be used, can produce undesirable complications. The use of medical devices such as stents, guide wires, pacing leads, catheters, or balloons in patients, for example, can result in bacterial infection, blood clotting, tissue trauma, autoimmune rejection, and other harmful side effects.

In certain situations, the likelihood or severity of these complications can be reduced by applying a coating to the medical device prior to inserting or implanting the device into a patient. Such device coatings can enhance the capabilities of medical devices. Specifically, some coatings can be used to release drugs or increase the visibility of devices to imaging systems. Other coatings may add such properties as lubricity, biocompatibility, and antimicrobial or other action to device surfaces. Still other coatings may offer a combination of these properties. An additional advantage of coatings is their ability to achieve these properties and actions without altering the bulk material properties of the medical device.

For reasons relating to cost, secondary properties of the coatings, ease of the implantation procedure, and other considerations, it may be desirable to apply a coating to only a portion or selected portions of the device. It may also be desirable to create distinct regions of the device that demonstrate properties different in function, appearance, or performance than the properties of other regions of the device. Known masking techniques in use may comprise heat shrinkable tubing or wrapping tape around the device. Such are cumbersome to apply, may damage the device during removal, and are not conducive to automation. Therefore, there is a need for selectively applying a coating to distinct regions of structures such as medical devices that can be done efficiently and provide for easy removal.

SUMMARY OF THE INVENTION

The present invention relates to selectively applying a coating to distinct regions of a structure such as a medical device. Examples of the coating process for which the present invention may be suitable include, but are not limited to, dip coating, spray coating, plasma coating, vapor deposition, pad coating, piezo jet coating, dry or water-based coating, UV curing, single-phase or multiple-phase coating.

The coating sleeve, or several coating sleeves, may be fitted onto a device, thereby forming masked and non-masked regions. In an example embodiment, a coating sleeve performs regional masking on a device modified through the application of a coating. While the non-masked region receives an application of the coating, the coating is substantially prevented from being applied to the masked region of the device. In this manner the masked region is not modified in the manner in which the non-masked region is modified. In an embodiment, a coating sleeve performs global masking on a device modified through the application of a coating.

The coating sleeve may completely, substantially, or partially mask a region of a device. This allows the amount and pattern of the coating applied to the masked region of the device to be selectively varied. In an embodiment, regional masking of the device facilitates partial modification that result in desired patterns of coating application on the modified surface of the device.

In operation, grasping and pulling forces may be applied to the coating sleeve to expand the coating sleeve. In an embodiment this is accomplished by an expanding tool with grasping portions such as pinchers. The coating sleeve may then be positioned on the device. Once fitted around the device, the grasping and pulling forces may be removed so that the coating sleeve is self-secured to the device, thereby creating a masked region. After a coating has been applied to the device, the grasping and pulling forces can be reapplied to the coating sleeve so that the device can be easily removed from the coating sleeve. In certain embodiments, the expanding tool can remain attached to the attachment portions during coating of the device with fluid or other surface modification.

In another embodiment the embodiment may be removed by manually grasping and tearing off the sleeve. The polymer may be selected to be tearable and may selected such that the tearable characteristic is enhanced during the coating process, such as during an ultraviolet curing process.

A feature and advantage of the invention is that using an expanding tool that grasps the sleeves at tabs or flanges provides a system highly suitable for automation and efficient and expedient processing.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 6 is a cross-sectional view of the sleeve and tool of FIG. 5 actuated to expand the sleeve according to an embodiment of the invention.

FIG. 7 is a cross-sectional view of an elongate medical device.

FIG. 10 is a side view of an embodiment of a sleeve, such as shown in FIG. 1, on an elongate medical device for coating or surface modification in accord with the invention.

FIG. 11 is a side view of an embodiment of a sleeve, such as shown in FIG. 2, on an elongate medical device for coating or surface modification in accord with the invention.

FIG. 12 is a side view of an embodiment of a sleeve, such as is shown in FIG. 3 on an elongate medical device.

Figure 3:
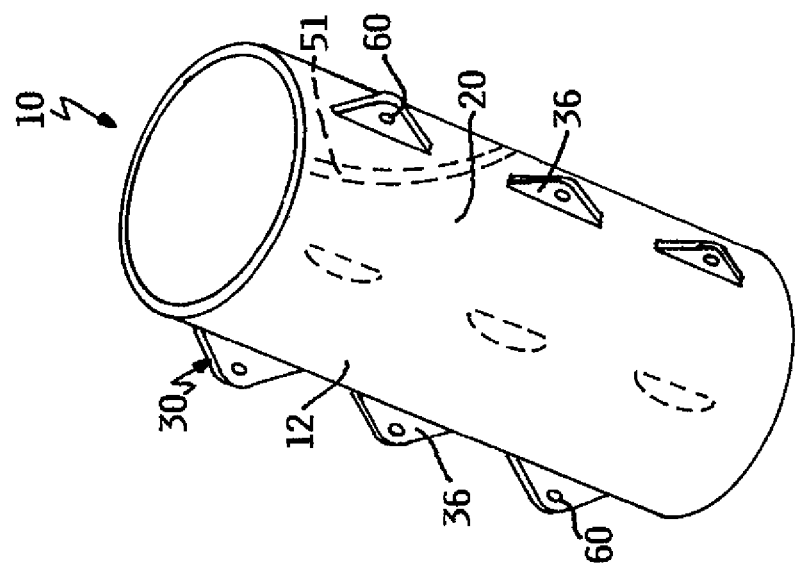
FIG. 3 is a perspective view of another sleeve according to an embodiment of the invention.

While the invention is amenable to various modifications and alternative forms, specifics thereof have been shown by way of example in the drawings and will be described in detail. It should be understood, however, that the intention is not to limit the invention to the particular embodiments described herein. On the contrary, the intention is to cover all modifications, equivalents, and alternatives falling within the spirit and scope of the invention as defined by the appended claims.

DETAILED DESCRIPTION OF THE INVENTION

An apparatus and a method for applying a coating to selected portions of a structure such as a medical device are disclosed. The present invention can be more readily understood by reference to FIGS. 1-11 and the following description. While the present invention is not necessarily limited to a particular coating sleeve, the present invention will be better appreciated using a discussion of exemplary embodiments in specific contexts. In addition, although the present invention is described primarily in the context of medical devices, the present invention may easily be adapted for use in applications involving devices, components, or apparatuses other than medical devices without departing from the spirit and scope of the invention.

Referring to FIGS. 1-11, coating sleeve 10 is disclosed according to various embodiments. Generally coating sleeve 10 is placed over a portion of a medical device to be modified through the application of a coating, see in particular FIGS. 4, 10 and 11. Coating sleeve 10 creates a masked region of the medical device. Similarly, multiple coatings sleeves 10 can be used to create multiple masked regions of the device. When the device is subject to application of a coating, the masked region is modified differently than non-masked regions of the device.

By altering the shape, structure, material, and other characteristics of coating sleeve 10, the region of the medical device masked by coating sleeve 10 can be selectively modified in any number of ways. In an example embodiment, the masked region is not modified in that coating material is not applied to the masked region of the device. In another embodiment, coating sleeve 10 permits substantial modification of the masked region when coating material is applied to the device. In another embodiment, coating sleeve 10 permits partial modification of the masked region when coating material is applied to the device. In another embodiment, coating sleeve 10 permits minimal modification of the masked region when coating material is applied to the device. In another embodiment, coating sleeve 10 permits patterned modification of the masked region when coating material is applied to the device. The length of coating sleeve 10, the number of coating sleeves 10, and the position of coating sleeve 10 on the medical device can also be varied to create different and/or multiple masked and non-masked regions. Coating sleeve 10 can therefore be adapted to effect modification of the masked region on the device in a variety of ways.

In creating a masked region on a device, coating sleeve 10 may be stretched so as to fit over and around a portion of the device and then relaxed to conform to the outer surface of the device. The shape and the elastomeric and frictional properties of the material of which coating sleeve 10 is made may enable coating sleeve 10 to self-secure to the medical device.

Figure 2:
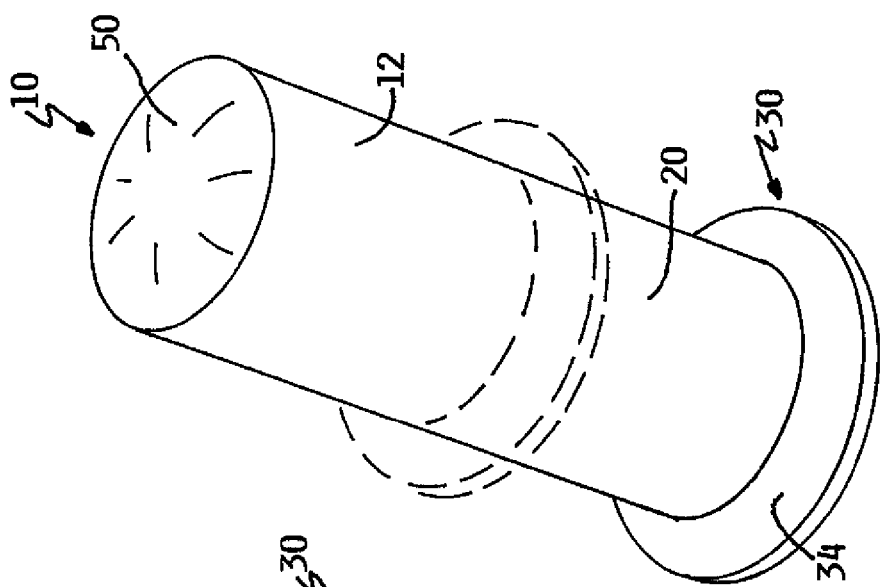
FIG. 2 is a perspective view of another sleeve according to an embodiment of the invention.
Figure 1:
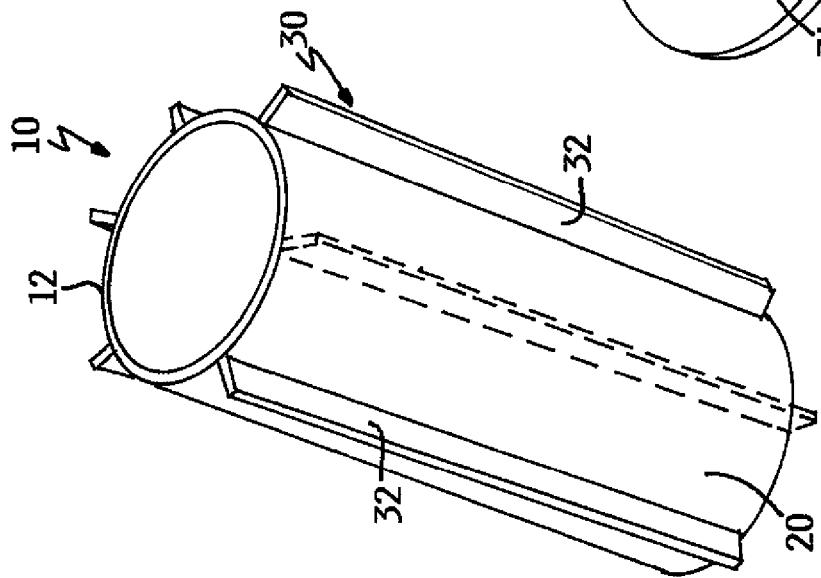
FIG. 1 is a perspective view of a sleeve according to an embodiment of the invention.

Referring to FIGS. 1-3, coating sleeve 10 generally comprises a tubular body portion 12 with a wall 20 and attachment portions configured as surface protrusions 30. Attachment portions 30 may have any number of shapes and be arranged in any number of patterns. In an embodiment, surface protrusions 30 may comprise flanges 34 coextensive with the body portion 12, as depicted in FIG. 2. In another embodiment, surface protrusions 30 may comprise ribs or tabs 32, 36 preferably in sets where individual members of each set are longitudinally in alignment and circumferentially spaced around the body portion. In another embodiment, surface protrusions 30 may comprise spaced-apart ribs or fins 36 positioned at different locations on wall 20 of coating sleeve 10. In an example embodiment, surface protrusions 30 are integral with wall 20. Coating sleeve 10 may also comprise cap 50. As shown in FIG. 3, a score line 51, or other recess in the surface of the body portion may be provided to facilitate tearing off the sleeve from the medical device after the coating of surface modification. An attachment portion may be grasped individually to commence the tear.

Figure 4:
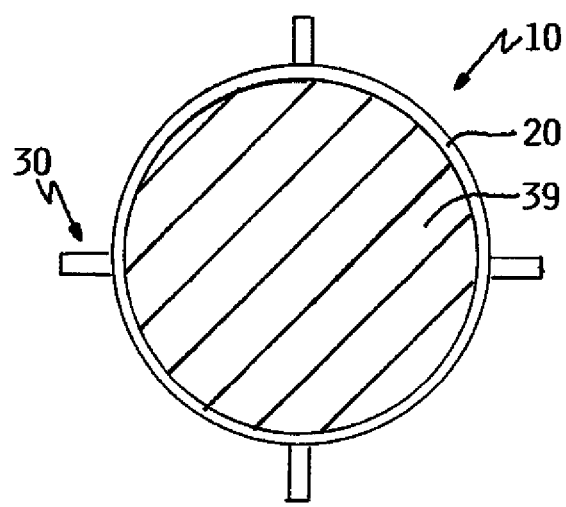
FIG. 4 is a cross-sectional view of a sleeve in place on an elongate medical device according to an embodiment of the invention.
Figure 5:
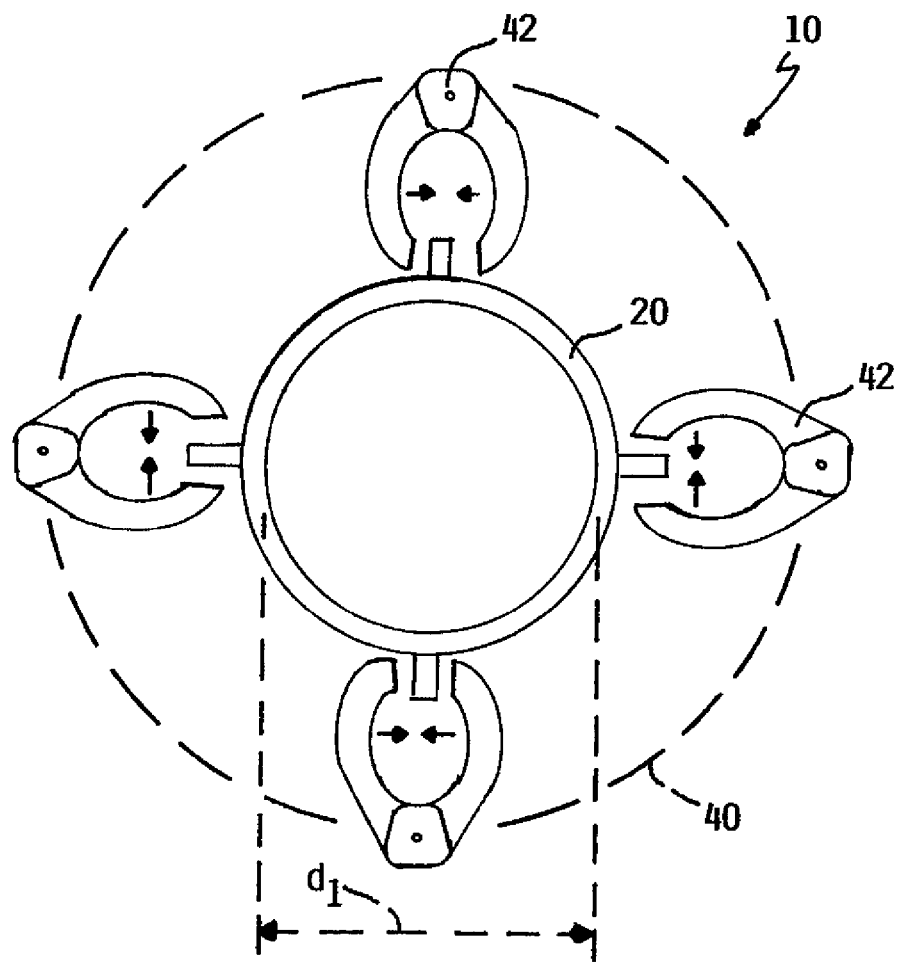
FIG. 5 is a cross-sectional view of a sleeve and an expanding tool according to an embodiment of the invention.

Referring to FIGS. 4-6, surface protrusions 30 of coating sleeve 10 may be used to facilitate manipulation of coating sleeve 10 to attach and remove the sleeve from the elongate medical device 39. The sleeve in FIG. 5 is shown in a retracted or "relaxed" state with an inside diameter d1 which is less than the diameter d2 of the elongate medical device 39. An expanding tool 40, preferably comprised of linked pinchers or clamping jaws 42, as indicated by the dashed circle, are movable simultaneously from an open ungripping position as shown in FIG. 5, to a clamping position as illustrated in FIG. 6. The clamping jaws are moved radially outward to expand the sleeve to the expanded or greater diameter state having a minimal inside diameter d3 that is greater than the outside diameter of the medical device at the region to be masked.

The "minimal diameter" of the sleeve when in the polygonal shape is the minimal dimensions spanning the interior through a center of the polygon. The straight-line arrows in FIG. 6 indicate the opposing forces to expand the sleeve. Such forces may also be applied to flanges 34. In an example embodiment, the pulling force is applied radially, that is, in a direction away from coating sleeve 10 and perpendicular to the geometric tangent from where surface protrusion 30 extends from wall 20. The attachment portions are released either in the expanded state with the clamping jaws at an outward position or the clamping jaws can be moved inwardly and then opened to release the attachment portions of the sleeve whereby the sleeve is engaged on the medical device 39 as illustrated in FIG. 4. The device surface may then be coated with a desired fluid or the surface otherwise treated such as by plasma radiation and the masked portion does not receive the coating fluid or radiation.

Manipulation of coating sleeve 10 by exerting grasping and pulling forces upon surface protrusions 30 cause coating sleeve 10 to expand to the greater diameter state of FIG. 6. In an example embodiment, this expansion may cause the inner circumference of wall 20 to become greater than the outer circumference of the device around which coating sleeve 10 is to be fitted In a preferred embodiment, the sleeve will take on a polygonal shape, where the attachment portions are pulled outwardly, see FIG. 6. Once coating sleeve is fitted around the device, the grasping and pulling forces may be relaxed or removed, thereby allowing coating sleeve 10 to create a masked region around a portion of the device. In other embodiments, separate arcuate members or longitudinally extending stiffening members may be disposed on or incorporated in the tubing portions to facilitate the expansion of the tubing portion.

Such members may be embedded in the wall of the sleeve or extend outwardly through the wall. The grasping and pulling forces may be applied in any number of ways in addition to the clamping described above. In an example embodiment, the grasping and pulling forces are manually applied, such as, for example, by a person. In another embodiment, the pulling forces and clamping or attachment forces are mechanically applied, such as by an extending tool that may be automated.

Figure 8:
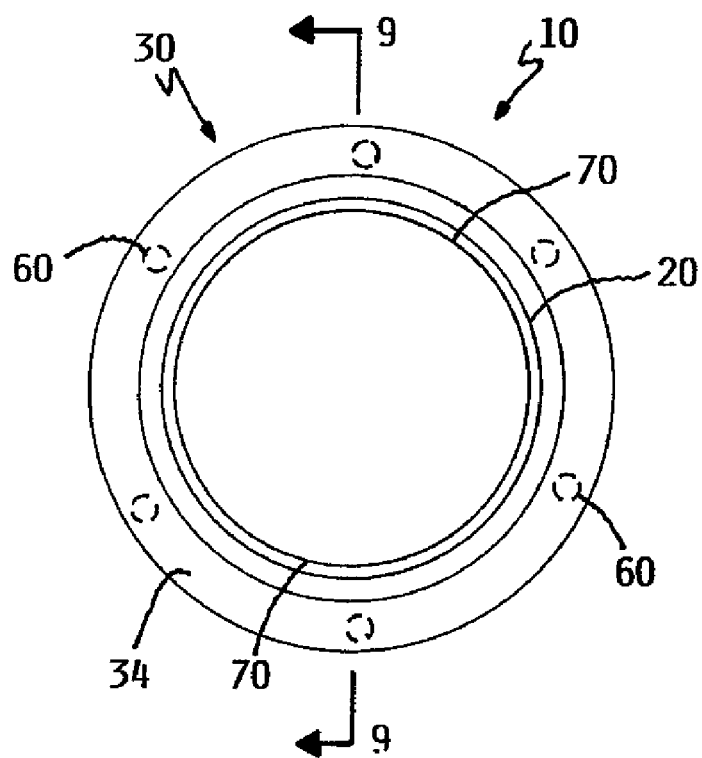
FIG. 8 is an end view according to an embodiment of the invention.
Figure 9:
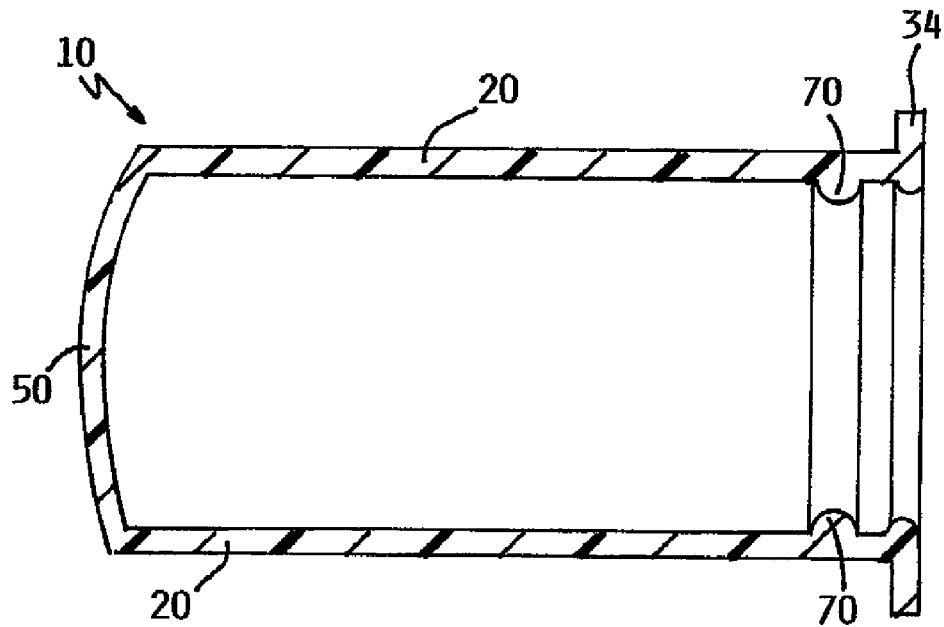
FIG. 9 is a side cross-sectional view taken at line 9-9 of FIG. 8.

Coating sleeve 10 may comprise additional features to facilitate or effect a desired modification of a device through the application of a coating. For example, surface protrusions may contain apertures 60, as depicted in FIGS. 3 and 8 providing loops. Apertures 60 may facilitate the grasping and pulling of surface protrusions 30 by members that are inserted into the apertures. Apertures 60 may also facilitate the positioning of coating sleeve 10 over and about the device and aid in removal of the device, for example to pull it off without expanding the sleeve. Coating sleeve 10 may also comprise integral cap 50. Cap 50 may facilitate positioning of coating sleeve 10 by providing a built-in stopping mechanism. Cap 50 may also protect an end portion of a medical device, such as the open portions of a catheter. Coating sleeve may also comprise rib 70 located on the inner surface of wall 20. Ribs may limit movement of coating sleeve 10 after coating sleeve 10 has been fitted onto a medical device and prevent migration of a coating material into the masked region. Such ribs may also be utilized on the other embodiments.

The chosen material of coating sleeve 10 may affect how the masked region of a medical device is modified as well as manipulation of coating sleeve 10. Generally, coating sleeve 10 is made of a material that allows it be stretched when gripped and manipulated. The material of which coating sleeve 10 is made may also possess memory that allows coating sleeve 10 to substantially return to its original shape. This would allow coating sleeve 10 to be stretched to fit over medical devices such as catheters, guide wires, stents, and pacing leads, and then subsequently return to the original form once the manipulation forces have been relaxed.

The physical properties of the material of which coating sleeve 10 is made may also change in response to environmental stimuli or physical manipulation. For example, elevated temperatures may be used to increase the elasticity of coating sleeve 10. In this manner, a reduction in temperature causing coating sleeve 10 to become more rigid may enhance the ability of coating sleeve 10 to self-secure around the device. Temperature variations may also be used in combination with or separately from memory materials to facilitate manipulation of coating sleeve 10 and enhance the ability of coating sleeve 10 to return to its original shape subsequent to being fitted around the device. The material of which coating sleeve 10 is made may also comprise a material that acts as a permeable media in allowing a selected amount of the coating material to modify the masked region of the device.

The medical devices, including components, which are created and for which the invention herein is applicable, are inserted into the body. For coronary applications the inner diameter of the relaxed sleeve may be from 0.006 inches to 0.060 inches. For other applications the medical device may be up to 3 cm in diameter of the sleeve approximately 2½ cm.

In an example embodiment, coating sleeve 10 is made from an elastomeric material. Specifically, coating sleeve 10 may be made from silicone, polyurethane, rubber, a thermoplastic, or a variety of other elastomers. Selection criteria for the material used to make coating sleeve 10 may include elasticity, elasticity ratios, compatibility with the material, shape and function of the device, the manner in which to material is manipulated in being fitted over the medical device, and the modification technique used to apply a coating to the device.

In operation, manipulation of coating sleeve 10 may be combined with a modification process that applies a coating to a structure such as a medical device. In an example embodiment, an operator inserts coating sleeve 10 into a fitting apparatus. A plurality of gripper jaws may exert grasping forces to grasp coating sleeve 10, advance coating sleeve 10 to a programmed location, and exert pulling forces to expand coating sleeve 10. The operator may then insert a distal end of the device into the apparatus until the distal end of the device reaches a desired location, which may be defined by a backstop. The fitting apparatus may then open the gripper jaws, causing coating sleeve 10 to close around the device and form a tight seal, thereby creating a masked region of the device. The operator may then remove the device from the fitting apparatus and load the device into a coating apparatus. The coating apparatus may then modify the device by applying a coating, such as, for example, through dipping or spraying. After the coating process is complete, the operator may remove the device from the coating apparatus and reinsert the device into the fitting apparatus. The fitting apparatus may then grasp and expand coating sleeve 10 such that an operator can remove the structure from the fitting apparatus without coating sleeve 10. In an embodiment, this method provides a non-modified region on a cardiac stent delivery catheter while dip coating the cardiac stent delivery catheter into a hydrophilic coating solution. Though not described, this method can also be used to selectively apply a coating to number of other devices or structures for a number of different purposes without departing from the spirit or scope of the invention.

Although various embodiments of the present invention have been disclosed herein for purposes of illustration, it should be understood that a variety of changes, alterations, and substitutions may be incorporated without departing from the spirit or scope of the present invention. The invention may be embodied in other specific forms without departing from the essential attributes thereof; therefore, the illustrated embodiments should be considered in all respects as illustrative and not restrictive. The claims provided herein are to ensure adequacy of the present application for establishing priority and for no other purpose.

What is claimed:

1. A method of coating or modifying the surface of an elongate medical device component comprising the steps of:
    attaching an expanding tool to a plurality of circumferentially spaced attachment portions projecting outwardly from an outer surface of a resilient tubular sleeve;
    radially expanding the resilient tubular sleeve by moving the plurality of circumferentially spaced attachment portions radially outward by pulling same with the expanding tool thereby putting the sleeve in a radially expanded state having a polygonal shape;
    positioning the tubular sleeve in the expanded state at a particular longitudinal location on the elongate medical device;
    allowing the plurality of circumferentially spaced attachment portions to retract radially inward whereby the tubular sleeve covers a portion of an outer circumferential surface of the elongate medical device at the particular longitudinal location while leaving other portions of the outer circumferential surface of the elongate medical device uncovered by the tubular sleeve;

at least one of modifying the outer circumferential surface or providing a coating to the outer circumferential surface of the elongate medical device after the sleeve has been positioned on the elongate medical device; and removing the sleeve from the elongate medical device.

2. The method of claim 1 wherein allowing the plurality of circumferentially spaced attachment portions to retract radially is accomplished by moving the attachment portions inwardly with the expanding tool attached to the attachment portions.

3. The method of claim 1 wherein allowing the plurality of circumferentially spaced attachment portions to retract radially is accomplished by releasing the attachment portions from the expanding tool when the sleeve is in the expanded state.

4. The method of claim 1 further comprising the step of attaching the expanding tool to the circumferentially spaced attachment portions by attachment of the circumferentially spaced attachment portions by the grasping tool.

5. The method of claim 1 wherein the circumferentially spaced attachment portions are configured as loops and the method further comprises the step of attaching the expanding tool to the circumferentially spaced attachment portions by hooking the loops by the grasping tool.

6. The method of claim 1 wherein the sleeve comprises a tubular body portion and the circumferentially spaced attachment portions are configured as circumferentially spaced tabs, and the method further comprises the step of grasping the tabs with individual pincher portions of the grasping tool.

7. The method of claim 1 further comprising the step of controlling the operation of the expanding tool by automation.

8. The method of claim 1 wherein the step of removing the sleeve from the elongate medical device includes tearing the sleeve from the medical device.

9. The method of claim 1 wherein the step of removing the sleeve from the elongate medical device includes attaching the expanding tool to the sleeve and radially expanding the sleeve.

10. A method of restricting application of coating fluids or restricting surface modification at a specific region on an outer surface of an elongate medical device, the method comprising the steps of:
providing a resiliently flexible tubular sleeve having a relaxed state with an inside diameter less than the outside diameter of at least a portion of the outer surface of the elongate medical device;
radially expanding the resilient tubular sleeve into an expanded state sized to fit over and be freely moved longitudinally on the outer surface of the elongate medical device;
positioning the sleeve over the elongate medical device at an exclusion region of the outer surface of the elongate medical device where the sleeve in the expanded state is not in engagement with the elongate medical device;
allowing the resilient tubular sleeve to retract onto the outer surface of the elongate medical device at the exclusion region of the elongate medical device thereby covering said region and leaving other portions of the outer surface of the elongate medical device uncovered by the sleeve; and
one of modifying the other portions of the outer surface and applying a coating to the other portions of the outer surface of the elongate medical device and utilizing the sleeve to prevent one of any coating of the elongate medical device at the exclusion region and modification of the exclusion region.

11. The method of claim 10 further comprising the step of grasping the sleeve at circumferentially spaced attachment portions extending outwardly from an outer surface of the sleeve before radially expanding the device.

12. The method of claim 11 wherein the step of radially expanding the resilient tubular sleeve further includes the step of expanding the sleeve into shape with a polygonal cross section.

13. The method of claim 10 further comprising the step of grasping the sleeve at the attachment portions by pinching said attachment portions with pincher members and moving the attachment portions radially outward.

14. The method of claim 10 further comprising removing the sleeve from the elongate medical device after the coating is applied by radially expanding the resilient tubular sleeve into an expanded state sized to fit over and be freely moved longitudinally on the elongate medical device.

15. The method of claim 10 further comprising removing the sleeve from the elongate medical device after the coating is applied by tearing the sleeve.

16. A method of processing an outer surface of an elongate medical device for prevention of coating at a particular region on the outer surface of the elongate medical device while allowing coating at other regions on the outer surface, the particular region having a maximum diameter, the method comprising the steps of:
radially expanding a resilient flexible sleeve from a lesser diameter state to a greater diameter state, the greater diameter state having a first minimal inside diameter;
positioning the sleeve in the greater diameter state over the particular region, the first minimal inside diameter being greater than the maximum diameter of the particular region of the elongate medical device;
causing the sleeve to retract to the lesser diameter state on the particular region of the elongate medical device whereby the particular region is engaged with and covered by the sleeve;
coating the surface of elongate medical device with a fluid or modifying the surface such that the particular region is prevented from being coated by the sleeve and the other regions on the outer surface are coated;
expanding the sleeve to the greater diameter state; and
removing the sleeve from the elongate medical device.

17. The method of claim 16 further comprising the step of expanding the sleeve to the greater diameter state by attaching an expanding tool to circumferentially spaced attachment portions extending outwardly from an outer surface of the sleeve and pulling the attachment portions radially outward by the expanding tool.

18. The method of claim 16 further comprising the step of expanding the sleeve to the greater diameter state by grasping circumferentially spaced tabs on the sleeve and pulling the attachment portions radially outward.

19. The method of claim 16 further comprising the step of utilizing an expanding tool to pinch the circumferentially spaced tabs and to pull the tabs radially outward whereby the sleeve takes a polygonal shape in the cross section at the tabs.

20. The method of claim 17 wherein the circumferentially spaced attachment portions are configured as loops and the method further comprises the step of attaching a expanding tool to the circumferentially spaced attachment portions by hooking the loops by grasping portions of the expanding tool.

21. The method of claim 16 wherein the step of removing the sleeve comprises the step of expanding the sleeve to the greater diameter state by attaching an expanding tool to circumferentially spaced attachment portions on the sleeve and pulling the attachment portions radially outward by the expanding tool.

22. The method of claim 16 wherein the step of removing the sleeve comprises the step of tearing the sleeve off of the medical device.

23. The method of claim 16 further comprising the step of controlling the operation of the expanding tool by automation.

* * * * *